(12) United States Patent
Morris

(10) Patent No.: US 10,232,118 B2
(45) Date of Patent: Mar. 19, 2019

(54) DRIVE ASSEMBLY FOR A DRUG DELIVERY DEVICE

(71) Applicant: Sanofi, Paris (FR)

(72) Inventor: Anthony Paul Morris, Coventry West Midlands (GB)

(73) Assignee: Sanofi, Paris (FR)

( * ) Notice: Subject to any disclaimer, the term of this patent is extended or adjusted under 35 U.S.C. 154(b) by 525 days.

(21) Appl. No.: 14/782,657

(22) PCT Filed: Apr. 8, 2014

(86) PCT No.: PCT/EP2014/056996
§ 371 (c)(1),
(2) Date: Oct. 6, 2015

(87) PCT Pub. No.: WO2014/166914
PCT Pub. Date: Oct. 16, 2014

(65) Prior Publication Data
US 2016/0045664 A1    Feb. 18, 2016

(30) Foreign Application Priority Data
Apr. 10, 2013 (EP) .................................... 13163102

(51) Int. Cl.
*A61M 5/31* (2006.01)
*A61M 5/315* (2006.01)
*A61M 5/20* (2006.01)

(52) U.S. Cl.
CPC ........ *A61M 5/315* (2013.01); *A61M 5/31511* (2013.01); *A61M 5/31543* (2013.01);
(Continued)

(58) Field of Classification Search
CPC ............................ A61M 5/315; A61M 5/3155; A61M 5/31511; A61M 5/31553; A61M 5/31583;
(Continued)

(56) References Cited

U.S. PATENT DOCUMENTS

| 533,575 A | 2/1895 | Wilkens |
| 4,865,591 A | 9/1989 | Sams |

(Continued)

FOREIGN PATENT DOCUMENTS

| CA | 2138528 | 2/1994 |
| CA | 2359375 | 7/2000 |

(Continued)

OTHER PUBLICATIONS

International Preliminary Report on Patentability in International Application No. PCT/EP2014/056996, dated Oct. 13, 2015, 6 pages.

(Continued)

*Primary Examiner* — Kevin C Sirmons
*Assistant Examiner* — Tezita Z Watts
(74) *Attorney, Agent, or Firm* — Fish & Richardson P.C.

(57) ABSTRACT

A drive assembly for a drug delivery device includes a drive mechanism comprising a piston rod and a drive member to drive the piston rod to dispense a dose of drug and a dose member coupled to the drive member. The assembly further comprises a return mechanism comprising a spring member. The assembly further comprises a movable member which is coupled to the spring member. In a setting, the movable member is coupled to the dose member and, the movable member is movable from an initial position to a dose set position, thereby biasing the spring member. In the dispensing, the drive member and the movable member are decoupled such that the drive mechanism is operable by the user by application of a driving force to the drive mechanism, wherein the spring member of the return mechanism drives the movable member independently of the driving force towards its initial position.

15 Claims, 8 Drawing Sheets

(52) U.S. Cl.
CPC .... *A61M 5/31551* (2013.01); *A61M 5/31575* (2013.01); *A61M 5/31585* (2013.01); *A61M 5/31541* (2013.01); *A61M 2005/2026* (2013.01); *A61M 2005/3126* (2013.01)

(58) Field of Classification Search
CPC .......... A61M 5/31585; A61M 5/31543; A61M 5/31551; A61M 5/31575; A61M 5/31541; A61M 2005/2026; A61M 2005/3126; A61M 2005/3125; A61M 2205/581; A61M 2205/582; A61M 2205/583; A61M 5/31555; A61M 5/31556–5/31563; A61M 5/31573; A61M 5/3158
See application file for complete search history.

(56) References Cited

U.S. PATENT DOCUMENTS

| | | |
|---|---|---|
| 5,092,842 A | 3/1992 | Bechtold et al. |
| 5,226,895 A | 7/1993 | Harris |
| 5,226,896 A | 7/1993 | Harris |
| 5,244,465 A | 9/1993 | Michel |
| 5,279,586 A | 1/1994 | Balkwill |
| 5,304,152 A | 4/1994 | Sams |
| 5,320,609 A | 6/1994 | Haber et al. |
| 5,378,233 A | 1/1995 | Haber et al. |
| 5,383,865 A | 1/1995 | Michel |
| 5,391,157 A | 2/1995 | Harris et al. |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,807,346 A | 9/1998 | Frezza |
| 5,820,602 A | 10/1998 | Kovelman et al. |
| 5,851,079 A | 12/1998 | Horstman et al. |
| 5,921,966 A | 7/1999 | Bendek et al. |
| 5,957,896 A | 9/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,562,006 B1 | 5/2003 | Hjertman et al. |
| 6,613,023 B2 | 9/2003 | Kirchhofer et al. |
| 6,699,224 B2 | 3/2004 | Kirchhofer et al. |
| 6,899,698 B2 | 5/2005 | Sams |
| 6,932,794 B2 | 8/2005 | Giambattista et al. |
| 6,936,032 B1 | 8/2005 | Bush, Jr. et al. |
| 7,169,132 B2 | 1/2007 | Bendek et al. |
| 7,241,278 B2 | 7/2007 | Moller |
| 7,678,084 B2 | 3/2010 | Judson et al. |
| 7,955,303 B2 * | 6/2011 | Burren .................. A61M 5/24 604/136 |
| 8,187,233 B2 | 5/2012 | Harms et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0097883 A1 | 5/2004 | Roe |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0016143 A1 | 1/2007 | Miller et al. |
| 2007/0129687 A1 * | 6/2007 | Marshall ................. A61M 5/20 604/207 |
| 2009/0275916 A1 | 11/2009 | Harms et al. |
| 2009/0318865 A1 * | 12/2009 | Moller .............. A61M 5/31553 604/135 |
| 2010/0324494 A1 | 12/2010 | Plumptre |
| 2012/0029443 A1 | 2/2012 | Holmqvist |
| 2012/0277683 A1 | 11/2012 | Moller |

FOREIGN PATENT DOCUMENTS

| | | |
|---|---|---|
| EP | 0496141 | 7/1992 |
| EP | 0 525 525 | 2/1993 |
| EP | 0897729 | 2/1999 |
| EP | 0937471 | 8/1999 |
| EP | 0937476 | 8/1999 |
| GB | 0304822.0 | 3/2003 |
| GB | 0304823.8 | 11/2017 |
| JP | H5-1993-503645 | 6/1993 |
| JP | 2004/503303 | 2/2004 |
| JP | 2012-522547 | 9/2012 |
| JP | 2012-528633 | 11/2012 |
| JP | 2013-511300 | 4/2013 |
| WO | WO 93/07922 | 4/1993 |
| WO | WO 93/24160 | 12/1993 |
| WO | WO 1999/038554 | 8/1999 |
| WO | WO 2001/010484 | 2/2001 |
| WO | WO 01/95959 | 12/2001 |
| WO | WO 02/030495 | 4/2002 |
| WO | WO 02/092153 | 11/2002 |
| WO | WO 03/080160 | 10/2003 |
| WO | WO 2006/084876 | 8/2006 |
| WO | WO 2008/058665 | 5/2008 |
| WO | WO 2013/034651 | 3/2013 |

OTHER PUBLICATIONS

International Search Report and Written Opinion in International Application No. PCT/EP2014/056996, dated May 14, 2014, 8 pages.
Rote Liste, "50. Hypophysen-, Hypothalamushormone, andere regulatorische Peptide u. ihre Hemmstoffe," Chapter 50, ed. 2008, 20 pages.
"Pen-injectors for medical use—Part 1: Pen-injectors—Requirements and test methods," International Standard, reference No. ISO 11608-1:2000(E), first edition Dec. 15, 2000, 32 pages.

* cited by examiner

DRIVE ASSEMBLY FOR A DRUG DELIVERY DEVICE

CROSS-REFERENCE TO RELATED APPLICATIONS

This application is a U.S. national stage application under 35 USC § 371 of International Application No. PCT/EP2014/056996, filed on Apr. 8, 2014, which claims priority to European Patent Application No. 13163102.0, filed on Apr. 10, 2013, the entire contents of which are incorporated herein by reference.

The present disclosure relates to a drive assembly for a drug delivery device, e.g. an injector-type device and/or a pen-type device.

A drug delivery device is, for example, known from WO 2008/058665 A1.

It is an object of the present disclosure to provide an assembly of one or more components which facilitate an operation of a drug delivery device.

This object is achieved by the subject-matter of the independent claim. Advantageous embodiments and refinements are subject-matter of the dependent claims.

One aspect of the present disclosure relates to a drive assembly for a drug delivery device. The drive assembly comprises a housing having a proximal end and a distal end. The "distal end" of the drug delivery device or a component of the drug delivery device shall mean the end which is closest to the dispensing end of the drug delivery device. The "proximal end" of the drug delivery device or a component of the drug delivery device shall mean the end which is furthest away from the dispensing end of the drug delivery device.

A further aspect of the present disclosure relates to a drug delivery device comprising the drive assembly.

The drive assembly further comprises a drive mechanism. The drive mechanism further comprises a piston rod. The drive mechanism further comprises a drive member to drive the piston rod to dispense a dose of drug. The drive assembly further comprises a dose member coupled to the drive member. The dose member is movable to set the dose of the drug. The coupling between the dose member and the drive member is, preferably, configured such that, when the dose member is moved to set the dose, also the drive member is moved, preferably in the same direction. The drive assembly further comprises a return mechanism comprising a spring member. Particularly, the return mechanism is provisioned to return or reset further components of the drive assembly or the drug delivery device during an operation of the drug delivery device. The drive assembly further comprises a movable member which is coupled to the spring member. The drive assembly is configured such that, in a setting mode of operation of the drive assembly, the movable member is coupled to the dose member. During setting of a dose, the movable member is movable from an initial position to a dose set position. Thereby, the spring member is biased. When the movable member is in the dose set position, the dose member is actuatable by a user to switch the drive assembly from the setting mode to a dispensing mode of operation of the drive assembly. The drive assembly is preferably configured such that the dose member can be manipulated, preferred manually, by the user, such as manually moved, by the user. According to this embodiment, the user is enabled to easily and selectively operate the device, such as to set or dispense a dose and/or to switch the drive assembly from the setting mode to the dispensing mode of operation.

In an embodiment, the drive assembly is configured such that in the dispensing mode of operation, the drive member and the movable member are decoupled such that the drive mechanism is operable by the user by application of a driving force to the drive mechanism. The driving force is preferably applied by the user via the dose member. Preferably, the driving force is further manually applied by the user, i.e. by the physical strength of, e.g., the user's hand only.

In an embodiment, the return mechanism is configured to drive the movable member independently of the driving force towards the initial position of the movable member.

As an advantage, the force necessary to drive the return mechanism does not need to be expended by the user, e.g. during dispensing of a dose in a dispensing operation. Thereby, the driving force which may be necessary to drive the drive mechanism can be kept small such that the user can easily dispense a dose of drug from the drug delivery device. Furthermore, the drive mechanism of the device may be embodied less susceptible to frictional forces such that the length or axial extension of the device can be reduced. Thereby, in turn, operability of the device can be improved.

An operation of the drug delivery device may particularly relate to a dose setting operation and a dose dispensing operation of the drug delivery device.

In an embodiment, the spring member is a torsion spring. According to this embodiment, it is enabled that the spring member is biased when a component coupled or connected to the torsion spring is rotated with respect to a component which is also coupled to the torsion spring. As a further advantage, the biasing of the spring member can be carried out within a comparatively small axial section of the drug delivery device such that an axial length or extension of the drug delivery device may be kept small. Thereby, operability of the drug delivery device can be further increased.

In an embodiment, the drive assembly is configured such that, during setting of a dose, the movable member rotates in a first direction with respect to the housing. In this way, it may be achieved that, during setting of a dose, the spring member is biased, as the movable member is coupled to the spring member.

In an embodiment, the drive assembly is configured such that during dispensing of the dose, the movable member rotates in the second direction, opposite to the first direction, with respect to the housing. In this way, it may be achieved that, during dispensing of a dose, the spring member drives the movable member towards its initial position. Beside the rotation of the movable member, the movable member may also be moved axially during its travel from the initial position to the dose set position.

The initial position may relate to a position of the drug delivery device in which no dose has yet been set or to a zero dose position corresponding to a state of the drug delivery device, wherein no dose is set. The dose set position may relate to the position in which a dose of drug is set.

In an embodiment, the dose member is rotationally locked with respect to the drive member. Thereby, it may be achieved that when the user actuates, e.g. rotates the dose member during setting of a dose, also the drive member is rotated, e.g. with respect to the housing. Thereby, also the drive member may be brought into a dose set position.

In an embodiment, the drive assembly comprises a releasable clutch mechanism. The releasable clutch mechanism is configured such that, in the setting mode of operation, the dose member is rotatable with respect to the housing. The user may thus set a dose by manually rotating the dose member with respect to the housing. The releasable clutch mechanism is further configured such that, in the dispensing mode of operation, a clutch feature interacts with a complementary clutch feature such that the dose member is rotationally locked with respect to the housing. The clutch feature is, preferably, provided by the drive member. The clutch feature may be a protrusion which is unitarily formed by the drive member. The clutch feature may further be flexed inwardly with respect to the drive member. The complementary clutch feature may be provided by a further component of the drive assembly. Preferably, the complementary clutch feature is provided by the housing or a component fixed thereto.

In an embodiment, the housing is formed by a main housing part and an inner housing which is connected or rigidly fixed to the main housing part.

In an embodiment, the drive member comprises a protrusion, e.g. a flexible protrusion for forming the clutch feature. The protrusion may pass over splines of, e.g. the inner housing. For passing over the splines, the protrusion may need to be flexed or deflected radially inwardly. Said splines may, thereby, form the mentioned complementary clutch feature.

In the dispensing mode of operation, said protrusion may be prevented from passing over the spline feature of the complementary clutch feature in that, e.g. the dose member or a feature thereof may be arranged with respect to the drive member such that the protrusion is prevented from deflecting such that said protrusion cannot pass over the splines of the inner housing.

In an embodiment, the movable member is threadedly coupled to the housing. The drive assembly is configured such that an axial travel of the dose member during setting of the dose is defined by the thread, particularly by the lead of the thread which establishes the threaded coupling of the movable member and the housing. Said thread coupling may further define an axial distance by which the movable member and/or the dose member is moved axially with respect to the housing, when a dose of drug is set.

Preferably, the lead of the thread coupling between the housing and the movable member equals that of a threaded coupling between the piston rod and the drive member (see also below).

In an embodiment, the drive assembly is configured such that, in the dispensing mode of operation, the driving force applied by the user is transferred to the piston rod via the drive mechanism to drive the piston rod in the distal direction with respect to the housing. Thereby, distal movement of the drive member which may be transferred in that the user manually presses the dose member distally, may further be transferred to the piston rod. The piston rod may be coupled to a piston. Said piston may be arranged within a cartridge containing a drug. The piston may be axially constrained to the piston rod. When the piston rod is moved distally, also the piston may be moved distally with respect to the cartridge such that a dose of drug can be dispensed from the drug delivery device.

The drug delivery device may be a variable dose device. The drug delivery device may further be a disposable device such that it is designed for single use only. To this effect, it may be delivered to the user in a fully assembled condition ready for first use. Alternatively, the device may be a reusable device. The doses of drug of the drug delivery device may be user-selectable.

In an embodiment, the drug delivery device comprises a needle or a needle assembly. Through said needle or needle assembly, a drug or medical substance which may be retained in the cartridge, can be dispensed from the drug delivery device.

In an embodiment, the movable member and the dose member are coupled via a releasable rotational locking mechanism. The drive assembly is configured such that, in the setting mode of operation, the releasable rotational locking mechanism is engaged such that the movable member and the dose member are rotationally locked. The drive assembly is further configured such that when, in a setting mode of operation, the movable member is in the dose set position and the user moves the dose member distally, the releasable rotational locking mechanism is disengaged such that the movable member and the dose member are free to rotate with respect to each other and the drive assembly is switched to the dispensing mode of operation. According to this embodiment, the user may introduce a dispensing operation or dispense a set dose of drug by a manipulation of the dose member. Preferably, the drive assembly is configured such that, when the user has moved the dose member distally, and he keeps pressing the dose member distally, the set dose is dispensed from the device within the same action by the user.

In an embodiment, the drive assembly is configured such that the energy stored in the spring member, when the movable member is in the dose set position, is used to drive the return mechanism and to drive a feedback mechanism operable to provide audible, visual and/or tactile feedback when the dose is being dispensed. The feedback mechanism may be a dispense clicker mechanism.

In an embodiment, the feedback mechanism is formed by the movable member and the dose member. During dose dispensing, the feedback mechanism may provide primarily audible feedback, informing the user that drug is being dispensed. Thereby, e.g. flexible arms provided by the movable member and a toothing provided by the dose member may provide for said audible feedback. Relative rotation may only be allowed in one relative direction of the movable member and the dose member. The feedback mechanism may be configured to provide for a single audible click for every unit of drug which is dispensed from the device.

In an embodiment, the driving assembly comprise a further feedback mechanism. The further feedback mechanism may be a setting clicker mechanism. The further feedback mechanism may be formed by the protrusion mentioned above which, when it passes over the spline feature of the complementary clutch feature, provides for an audible, visual and/or tactile feedback. According to this embodiment, a safe operation of the drug delivery device may be achieved, as the user is given feedback once the set dose is increased by, e.g. one unit of drug.

In an embodiment, the drive assembly comprises a display member, wherein the display member is rotationally locked with respect to the housing, and wherein an axial distance by which the display member is moved is greater than an axial distance by which the dose member is moved, when the movable member is moved from the initial position to the dose set position. This provides the advantage of an increased operability of the drive assembly or the drug delivery device. As manual dexterity of a user may be limited, a shorter axial travel of the dose member and, in this way, a smaller device length is desirable, as such devices can be operated easier. However, the distance by which the display member is moved under the given condition may be required to be larger to allow for the indicia of the indication member to be visible through the display member window.

As an advantage of the previous embodiment, said axial distance by which the dose member is moved, is kept small, as, thereby, also the axial length of the drug delivery device may be kept small while the axial distance by which the display member is moved, is advantageously greater.

In an embodiment, the drive assembly comprises an indication member. By the provision of the display member and the indication member, it may be enabled that dose information is indicated to the user during an operation of the drug delivery device in a user-friendly and safe way.

In an embodiment, the display member comprises a display member window. Through the display member window, dose information may be displayed to the user.

In an embodiment, the indication member comprises indicia. Said indicia may be arranged helically around an outer surface of the indication member. Preferably, the indicia provide for dose information, such as units or quantities of drug to be dispensed from the drug delivery device.

In an embodiment, the indication member and the display member have a sleeve-like shape. In this way, a large number of indicia may be provided by the indication member. Furthermore, the indication member may at least partly be retained in the display member.

In an embodiment, the drive assembly is configured such that, during an operation of the drive assembly, the display member is moved axially with respect to the indication member such that different indicia are visible through the display member window.

Thereby, the indicia may be identified by the user. The drive assembly is, preferably, configured such that, during the operation of the drug delivery device, the display member may be moved axially with respect to the indication member. The indicia may, furthermore be arranged on the indication member such that only one indicium is visible through the display member window at a time, thereby indicating the actually set or dispensed dose, i.e. an actual dose status of the device.

In an embodiment, the display member is rotationally locked with respect to the housing. This provides the advantage that the actual dose status of the device may be indicated through the display member window at a constant rotational position with respect to, e.g., the housing. This, in turn, means that the user can easily and reproducibly identify dose information of the drug delivery device.

In an embodiment, the dose member comprises an inner section. The drive assembly is configured such that, when the movable member is in the dose position, a proximal end section of the display member is retained in the inner section. As an advantage of this embodiment, a proximal section of the display member may be accommodated by the inner section, even if the axial distance by which the display member is moved exceeds that one of the dose member, during setting of a dose.

In an embodiment, the drive assembly is configured such that, when the movable member is in the initial position, the proximal end section is arranged outside of the inner section.

In an embodiment, a guiding element of the drive assembly comprises a first thread section with a first lead and a second thread section with a second lead, wherein the second lead is greater than the first lead. This embodiment allows that a component which is threaded to the guiding element may be moved by different axial distances, for instance when said component is coupled, particularly threaded to the guiding element. The guiding element may be or be provided by the drive member.

In an embodiment, the drive assembly comprises a last dose member which is operable to be moved away from a start position towards an end position when the dose is being increased. Accordingly, the last dose member may be moved away from the end position towards the start position when a previously set or increased dose is decreased. The last dose member is configured to interact with the first thread section when the last dose member is arranged in or near the start position. Thereby, a relative axial movement between the last dose member and the guiding element is determined by the first lead.

In an embodiment, the last dose member is configured to interact with the second thread section when the last dose member is arranged in or near the end position. The term "near" the start and the end position shall refer to a position of the last dose member, wherein the last dose member engages the first and the second thread section, respectively.

According to this embodiment, it may be achieved that when the guiding element is rotated with respect to the last dose member, the last dose member moves by a greater axial distance when it is arranged in or near the end position, as the second lead is greater than the first lead.

In an embodiment, the last dose member is configured to threadedly engage the first thread section and the second thread section. Thereby, it may be achieved that the last dose member may subsequently threadedly engage the first thread section and the second thread section, when a dose of drug is set. Depending on the relative position of the last dose member and the guiding element, the last dose member may then engage the first or the second thread section such that the axial distance by which the last dose member is moved with respect to the guiding element—said axial distance being determined by the first and the second lead—is also determined by said relative axial position of the last dose member and the guiding element.

The first thread section may be a distal thread section of the guiding element. The second thread section may be a proximal thread section of the guiding element.

In an embodiment, the drive member comprises a drive member stop feature. By the drive member stop feature, a rotational drive member stop may be defined.

In an embodiment, the last dose member comprises a last dose stop feature. By the last dose stop feature, a rotational dose member stop may be defined.

In an embodiment, the last dose stop feature is configured to form a rotational stop with the drive member stop feature when the last dose member interacts with the second thread section such that a further increase of the set dose is prevented. Preferably, the drive member stop feature and the last dose stop feature abut when the last dose member is arranged in the end portion such that a further increase of the set dose is prevented.

The term "lead" relates to the axial distance by which a component, the movement of which is defined by the respective thread, is moved when rotated by a single revolution. The term "pitch" relates to the axial distance between adjacent thread courses or windings. For a single start thread the pitch is the same as the lead.

In an embodiment, the first thread section and the second thread section are single start thread sections. This provides the advantage of a smaller lead for a given pitch as compared to multi-start thread section, for example.

In an embodiment, the outer diameter of the second thread section is larger than the outer diameter of the first thread section. The inner or minor diameters of the first thread section and the second thread section are, preferably, the same. This embodiment allows the second thread section to engage with a different internal thread, such as a thread of the last dose member, for example.

In an embodiment, the axial extension of the last dose stop feature is greater than a pitch or lead of the first thread section and less than a pitch of the second thread section. As an advantage, the rotational stop can be configured comparatively large and robust. In particular, an abutment or contact length of said rotational stop features can be embodied larger, with respect to axial extension, than the pitch of the first thread section. This allows for a more robust configuration of said rotational stop, wherein a further increase of the set dose can be reliably prevented when the last dose member is arranged in the end position. Preferably, the axial extension of the drive member stop feature is also greater than the pitch of the first thread section and less than the pitch of the second thread section.

In an embodiment, the last dose member is rotationally locked with respect to the housing. According to this embodiment, it may be achieved that the last dose member travels with respect to the drive member when a dose of drug is set, particularly when a dose is increased or a dose is decreased.

In an embodiment, the drive member is axially constrained with respect to the movable member. During dispensing of a dose, the spring member tends to rotate the movable member towards its initial position, along its threaded coupling with the housing. Due to the axial constraint between the movable member and the drive member, at least to a certain extent, the movable member drives or moves the drive member distally, when a dose of drug is dispensed from the drug delivery device. In this regard, the spring member may actuate or contribute to an auxiliary drive mechanism which is separate from the mentioned drive mechanism. A proximal face of the drive member and a distal face of the movable member may abut during dispensing of a dose. During setting of a dose, a marginal play may exist between said proximal face of the drive member and said distal face of the movable member.

In an embodiment, a first end of the spring member is connected to the housing and a second end of the spring member is connected to a distal end of the indication member. According to this embodiment, the general functionality of the drive assembly can be achieved most expedient, particularly in terms of a compact and simple device design.

In an embodiment, the movable member is rotationally locked with respect to the indication member. Thereby, it is achieved that a rotation of the indication member during an operation of the device is transferred to the movable member or vice versa. According to this embodiment, the general functionality of the drive assembly can be achieved most expedient, particularly in terms of a compact and simple device design.

In an embodiment, the piston rod comprises a first thread feature which matches to a drive thread feature of the drive member. Via the first thread feature and the drive thread feature, the piston rod and the drive member are preferably coupled such that a distal movement of the drive member with respect to the housing, which may occur during dispensing or delivery of the dose, can be transferred to a rotational and a distal movement of the piston rod.

In an embodiment, the piston rod comprises a second thread feature which matches a housing thread feature, wherein the first and the second thread features overlap or interfuse. According to this embodiment, the piston rod may, at the same time, be threaded to a housing component, preferably to the inner housing, and the drive member. By the interfusing configuration of the first and the second thread features of the piston rod, the ranges in which the piston rod respectively threadedly interacts with the housing and the drive member may axially overlap, such that a compact design of the drive assembly or the design can be achieved.

As the last dose member may be configured with a double thread in order to interact with the first and the second thread section, the last dose member occupies the shorter axial length as compared to the corresponding component in drug delivery devices not comprising such a last dose member and a guiding element with a first and a second thread section. Thereby, it is enabled that e.g. larger capacity medicament cartridges can be used without increasing the device length.

In an embodiment, the drive assembly is configured such that the ratio of the leads of the first and second thread features defines a mechanical advantage between an axial movement of the drive member and an axial movement of the piston rod when the dose is dispensed. The mechanical advantage is calculated by the sum of the leads of the first and the second thread feature divided by the lead of the second thread feature. Said mechanical advantage may relate to the distance by which the drive member is moved axially with respect to the housing and the axial distance by which the piston rod is moved distally with respect to the housing during dispensing of a dose. Said mechanical advantage may take values of e.g. 2:1 or 3:1.

The presented concept of the drive assembly allows for an embodiment of a drug delivery device, wherein the axial travel of the dose member for a given set dose is comparatively small. This is because frictional forces arising from a movement of the movable member and the indication member, for instance, may be expanded by the spring force or spring torque of the spring member during dispensing of a dose such that the driving force exerted by the user can be used to directly drive the drive mechanism via the drive member and the piston rod and no user force is required to be applied to a threaded interface to generate a torque to return the display assembly components. Thus, the thread engagement between the movable member and the inner housing may be provided with a comparatively small lead, whereby the axial length of the drug delivery device can be kept small, particularly in a state in which the maximum settable dose is set. A smaller axial length of the drug delivery device, in turn, leads to an increased operability and an improved ergonomic design of the drug delivery device.

The term "drug" or "medical substance", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28]Exendin-4(1-39),
des Pro36 [IsoAsp28]Exendin-4(1-39),
des Pro36 [Met(O)14, Asp28]Exendin-4(1-39),
des Pro36 [Met(O)14, IsoAsp28]Exendin-4(1-39),
des Pro36 [Trp(O2)25, Asp28]Exendin-4(1-39),
des Pro36 [Trp(O2)25, IsoAsp28]Exendin-4(1-39),
des Pro36 [Met(O)14 Trp(O2)25, Asp28]Exendin-4(1-39),
des Pro36 [Met(O)14 Trp(O2)25, IsoAsp28]Exendin-4(1-39); or
des Pro36 [Asp28]Exendin-4(1-39),
des Pro36 [IsoAsp28]Exendin-4(1-39),
des Pro36 [Met(O)14, Asp28]Exendin-4(1-39),
des Pro36 [Met(O)14, IsoAsp28]Exendin-4(1-39),
des Pro36 [Trp(O2)25, Asp28]Exendin-4(1-39),
des Pro36 [Trp(O2)25, IsoAsp28]Exendin-4(1-39),
des Pro36 [Met(O)14 Trp(O2)25, Asp28]Exendin-4(1-39),
des Pro36 [Met(O)14 Trp(O2)25, IsoAsp28]Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28]Exendin-4(1-39)-Lys6-NH2,
des Asp28 Pro36, Pro37, Pro38Exendin-4(1-39)-NH2,
H-(Lys)6-des Pro36, Pro38 [Asp28]Exendin-4(1-39)-NH2,
H-Asn-(Glu)5des Pro36, Pro37, Pro38 [Asp28]Exendin-4 (1-39)-NH2,
des Pro36, Pro37, Pro38 [Asp28]Exendin-4(1-39)-(Lys)6-NH2,
H-(Lys)6-des Pro36, Pro37, Pro38 [Asp28]Exendin-4(1-39)-(Lys)6-NH2,
H-Asn-(Glu)5-des Pro36, Pro37, Pro38 [Asp28]Exendin-4 (1-39)-(Lys)6-NH2,
H-(Lys)6-des Pro36 [Trp(O2)25, Asp28]Exendin-4(1-39)-Lys6-NH2,
H-des Asp28 Pro36, Pro37, Pro38 [Trp(O2)25]Exendin-4(1-39)-NH2,
H-(Lys)6-des Pro36, Pro37, Pro38 [Trp(O2)25, Asp28]Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28]Exendin-4(1-39)-(Lys)6-NH2,
H-(Lys)6-des Pro36, Pro37, Pro38 [Trp(O2)25, Asp28]Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28]Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28]Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28]Exendin-4(1-39)-(Lys)6-NH2,
H-(Lys)6-des Pro36, Pro37, Pro38 [Met(O)14, Asp28]Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28]Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28]Exendin-4(1-39)-NH2,
H-Asn-(Glu)5-des Pro36, Pro37, Pro38 [Met(O)14, Trp(O2) 25, Asp28]Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28]Exendin-4(S1-39)-(Lys)6-NH2,
H-Asn-(Glu)5-des Pro36, Pro37, Pro38 [Met(O)14, Trp(O2) 25, Asp28]Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features which are described herein above and below in conjunction with different aspects or embodiments, may also apply for other aspects and embodiments. Further features and advantageous of the subject matter of the disclosure will become apparent from the following description of the exemplary embodiment in conjunction with the figures, in which.

Figure 7A:
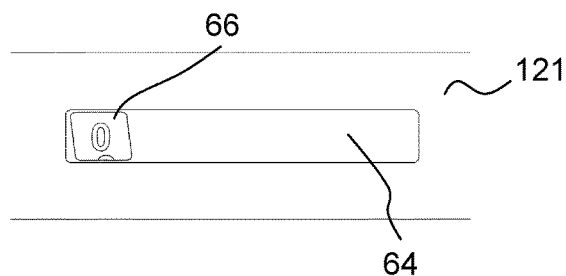
Figure 7B:
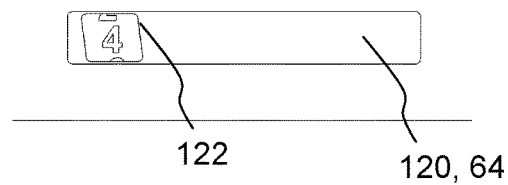
Figure 7C:
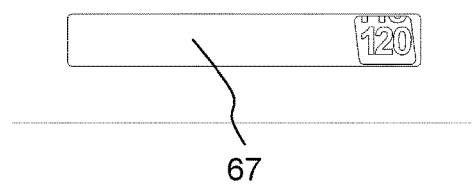

FIGS. 7A-C illustrate different states of a display assembly of the drug delivery device, respectively.

Figure 8:
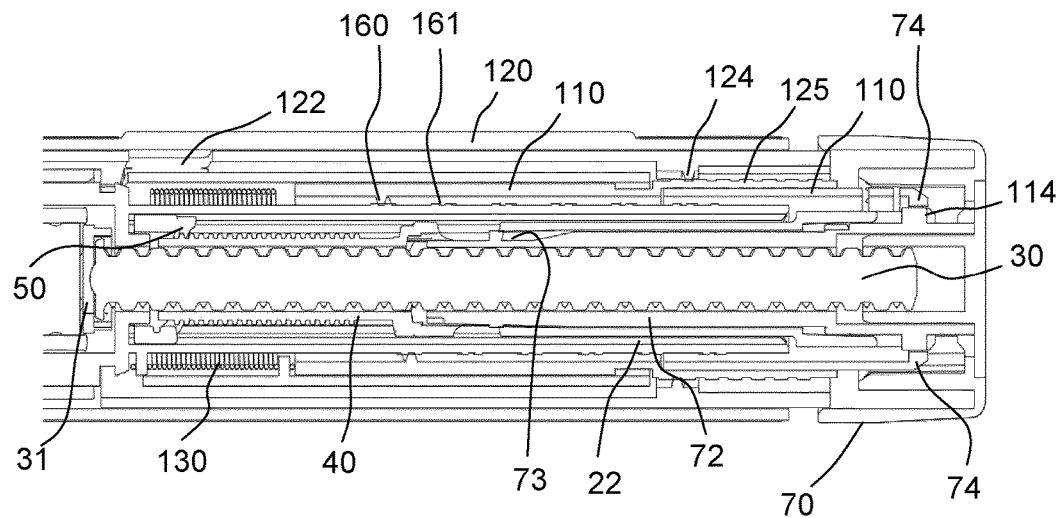

FIG. 8 shows a partial longitudinal section view of components of the drive mechanism of the drug delivery device.

Figure 9:
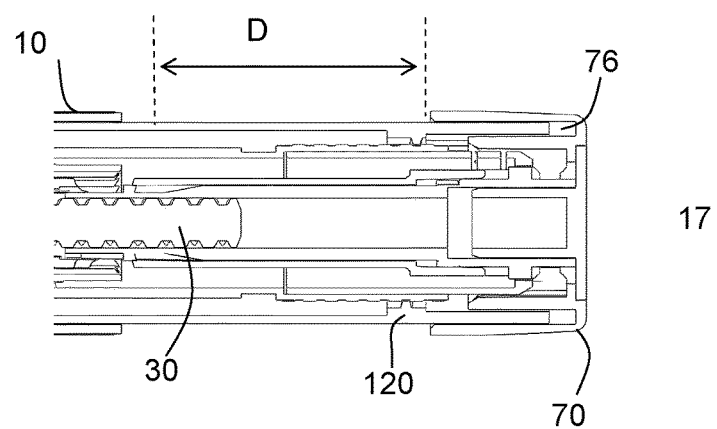

FIG. 9 shows a partial longitudinal section view of inner components of the drug delivery device.

Figure 10:
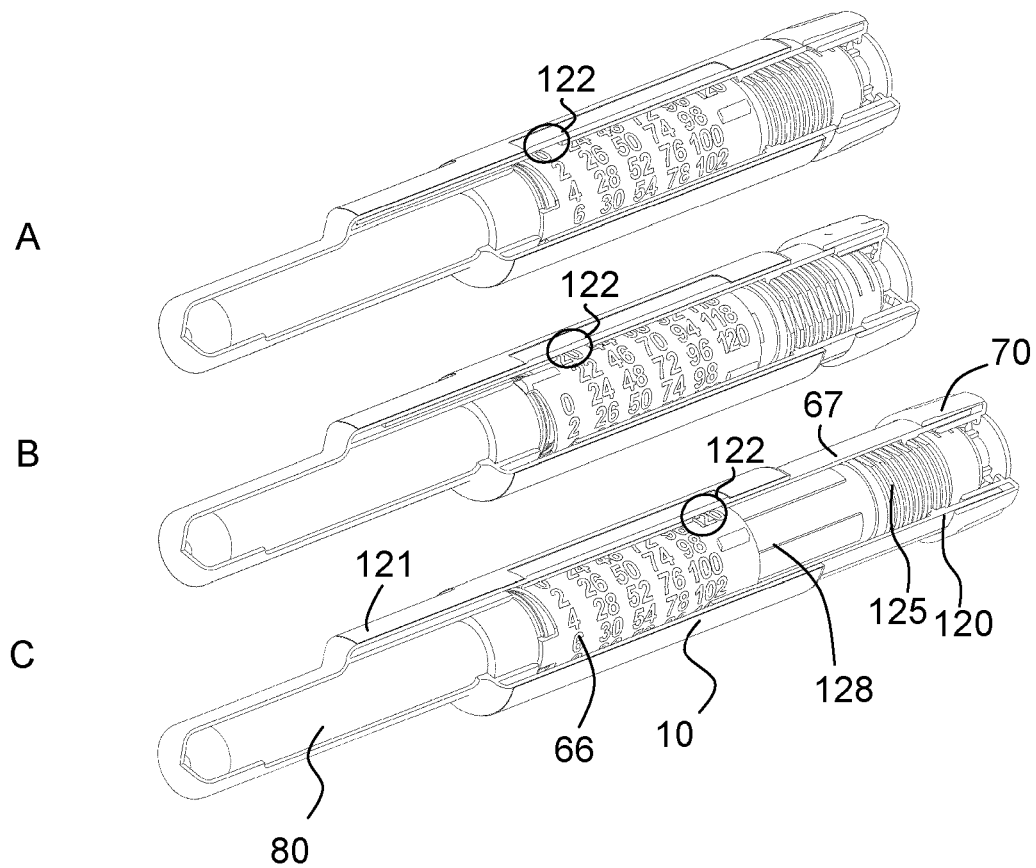

FIGS. 10A-C show a perspective view of components of a drug delivery device, respectively, wherein different states of the drug delivery device are depicted.

Figure 11:
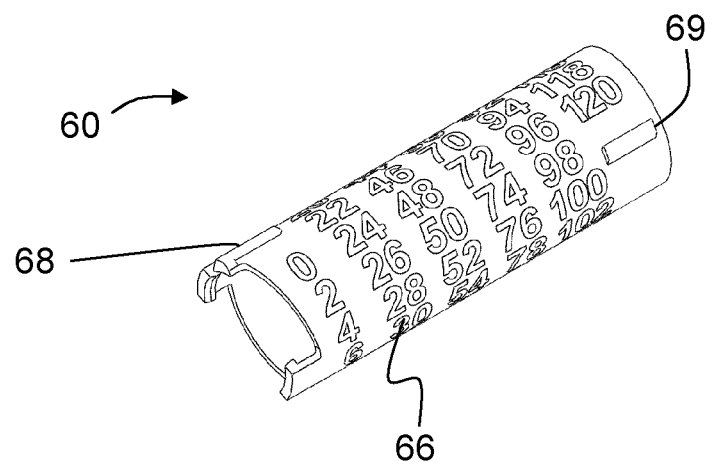

FIG. 11 shows a perspective view of an indication member of the drug delivery device.

Figure 12:
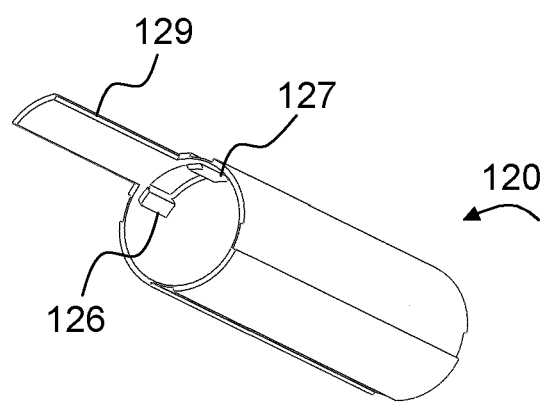

FIG. 12 shows a perspective view of a display member of the drug delivery device.

FIGS. 13A-C show a partial perspective view of components of the drug delivery device, respectively.

Figure 14:
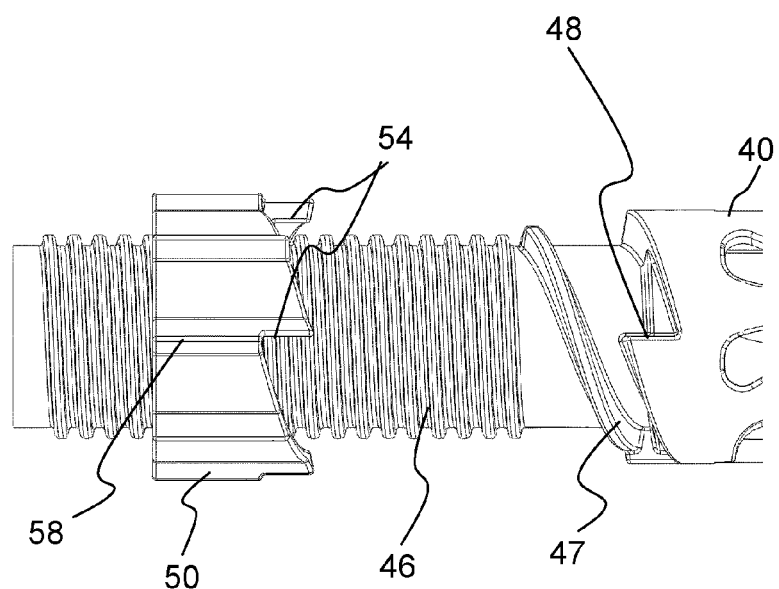

FIG. 14 shows a side view of a last dose member and parts of a drive member of the drug delivery device.

Figure 15:
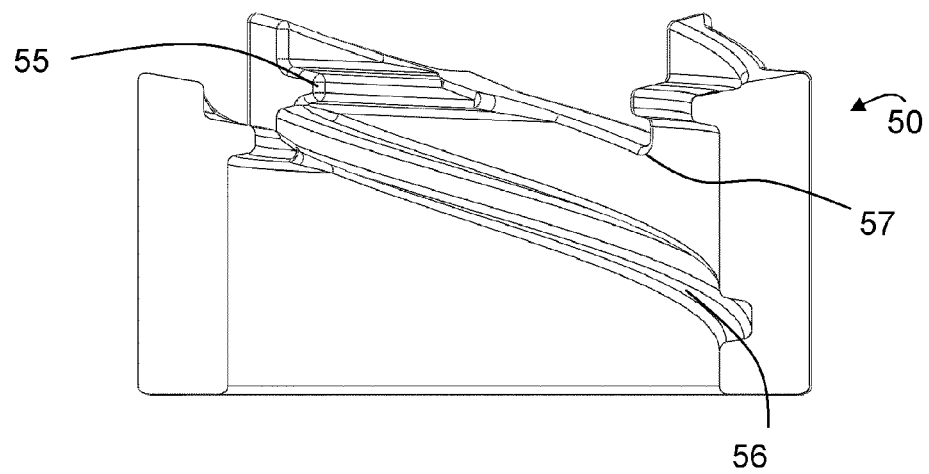

FIG. 15 shows a longitudinal section view of the last dose member of the drug delivery device.

Like elements, elements of the same kind and identically acting elements may be provided with the same reference numerals in the figures. Additionally, the figures may be not true to scale. Rather, certain features may be depicted in an exaggerated fashion for better illustration of important principles.

Figure 1:
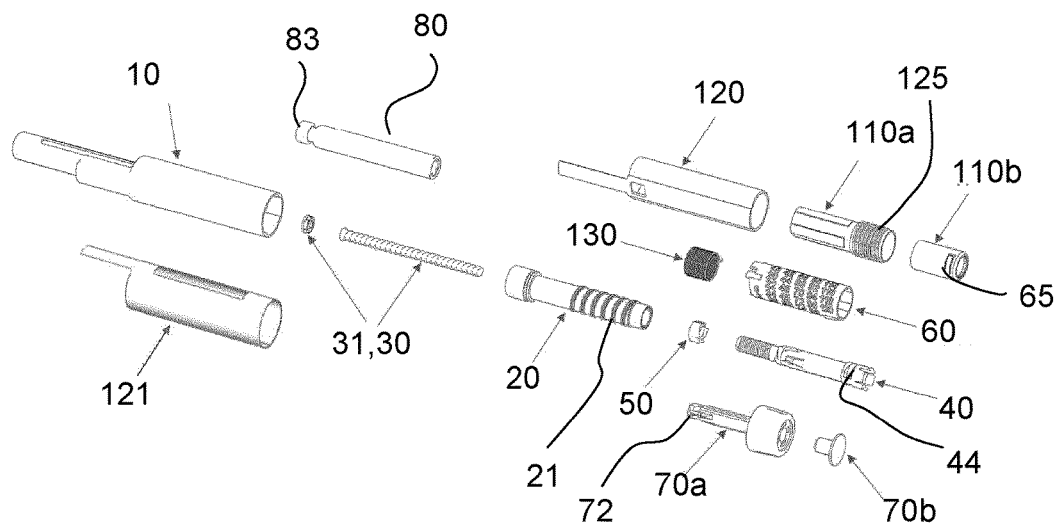
FIG. 1 shows an exploded view of components of a drug delivery device.

As shown in FIG. 1, the drug delivery device comprises a housing 10. The housing 10 may constitute an outer body of the drug delivery device 100. The housing 10 comprises a longitudinal axis which may coincide with the longitudinal axis x (cf. FIG. 2) of the drug delivery device 100. The drug delivery device 100 further comprises a label 121 which may be affixed to an outer surface of the housing 10. The label 121 may comprise an aperture which may define a housing window 123 when the label 121 is affixed to the housing 10. In a preferred embodiment, the outer housing 10 is transparent. Preferably, the label 121 is opaque.

Figure 2:
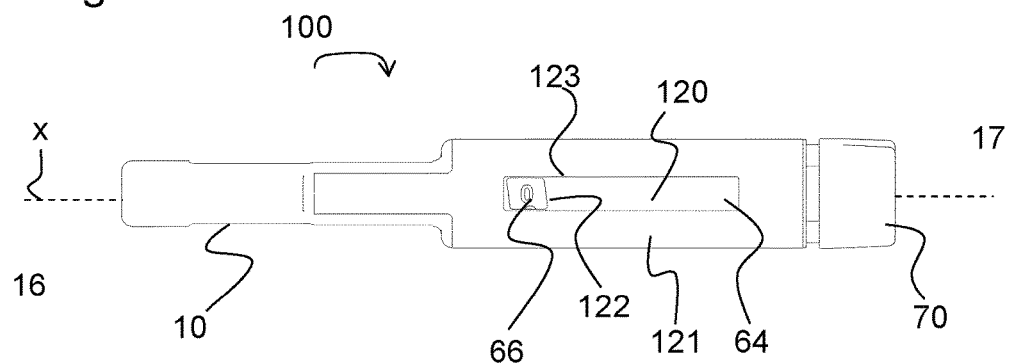
FIG. 2 shows a side view of the drug delivery device.

In FIG. 2, it is shown that the label 121 covers most of the housing 10 with the exception of the window 123. The outer housing part 10 is a generally tubular element having a distal part, which forms a cartridge holder for receiving cartridge 80, and a proximal part.

The drug delivery device 100 further comprises an inner body 20, a piston rod 30, a driver 40, a nut 50, an indication member 60 and a cartridge 80. The drug delivery device 100 may comprises additional components such as a needle arrangement comprising a needle hub and a needle cover.

The drug delivery device 100 further comprises a first button part 70a which, after an assembly of the drug delivery device 100, is preferably rigidly fixed to a second button part 70b in order to form a button 70 of the drug delivery device 100 (cf. in FIG. 1). When, in the following, it is referred to the button 70, it is referred to both components (70a and 70b) which are rigidly connected to each other. When referring to a dose member, it may also be referred to the button. As the same component is meant, the same reference numerals are used for the button and the dose member. The dose member may be the button.

The button 70 may have a surface allowing a user to easily grip the button 70.

The inner body 20 is a generally tubular element having different diameter regions. When referring to an inner housing, it may also be referred to the inner body. As the same component is meant, the same reference numerals are used for the inner body and the inner housing. The inner housing may be the inner body.

Figure 3:
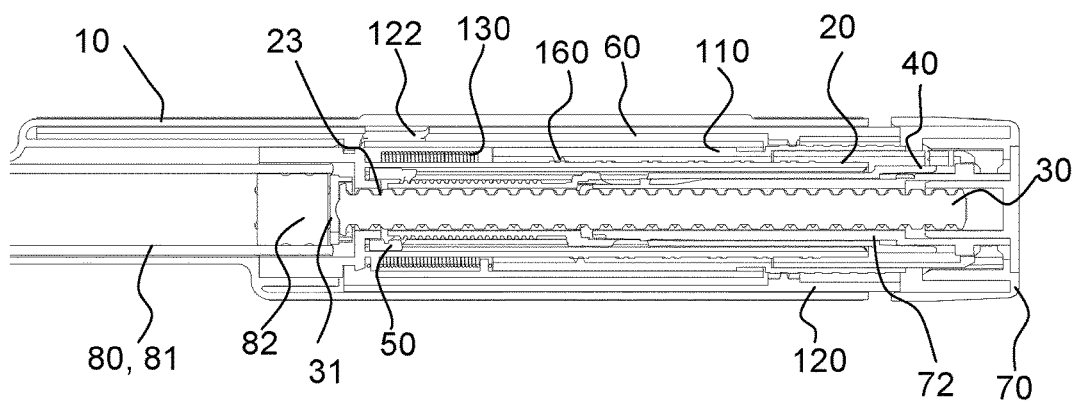
FIG. 3 shows a longitudinal section view of components of a drive mechanism of the drug delivery device.

As can be seen, e.g. in FIG. 3, the inner body 20 is received in the housing 10 and permanently fixed therein to prevent any relative movement of the inner body 20 with respect to the housing 10. An external thread 21 is provided on the outer surface of the inner body 20. Further, splines 22 are provided on the inner surface of the inner body 20 which are shown in FIG. 5, for example. As can be taken from FIGS. 3 and 4, the inner body 20 has near its distal end an inner thread 23.

The piston rod 30 is an elongate element having two external threads (not explicitly indicated) with opposite hand which overlap or interfuse each other. One of these threads engages the inner thread 23 of the inner body 20. The drug delivery device further comprises a bearing 31. As shown in FIG. 3, the bearing 31 may interact with the piston rod when the drug delivery device 100 is in an assembled state. The bearing 31 is separated from the piston rod 30 such that the bearing 31 remains seated on the distal end of the piston rod 30 to allow relative rotation between the bearing 31 and the piston rod 30.

The driver 40 is a generally tubular element having different diameter regions. When referring to a drive member, it may also be referred to the driver. As the same component is meant, the same reference numerals are used for the drive member and the driver. The drive member may be the driver. The driver 40 is rotationally locked to the button 70, e.g., via a corresponding spline engagement.

A distal region of the driver 40 has an external thread 46, as will be outlined below. An inner surface of the driver 40 has an inner thread (not explicitly indicated) engaging one of the external threads of the piston rod 30. The driver 40 surrounds the piston rod 30 and is at least partly located within inner body 20 when the device 100 is assembled (cf. FIG. 3). The driver 40 has a proximal opening which will be explained in more detail below. Further, a resilient finger 44 is provided on the driver 40 by a U-shaped cut in the skirt of the driver 40, as shown in FIG. 1. The finger 44 is allowed to flex in the axial direction and engages a button 70 (see below). In addition, a flexibly hinged protrusion 45 (cf. FIG. 8) is provided on the driver 40 by a similar cut-out in the skirt of the driver 40. The protrusion 45 may form or contribute to the function of a clutch feature. The protrusion 45 is allowed to flex radially inwardly. Protrusion 45 engages splines 22 of the inner body 20. The splines 22 may constitute a complementary clutch feature. The protrusion 45 and splines 22 additionally form a clicker arrangement that provides tactile and audible feedback to the user when setting or dialling doses. This clicker arrangement has the further functions of defining discrete positions for the indication member 60 when dialling and of providing a method of locking the rotation of the driver 40 and, hence, the dose member 70. This functionality may be provided by a releasable clutch mechanism being configured such that, in the setting mode of operation, the dose member 70 is rotatable with respect to the housing and, in the dispensing mode of operation, a clutch feature interacts with a complementary clutch feature such that the dose member 70 is rotationally locked with respect to the housing 10. During dialling, the button 70 is in an axial position relative to the driver 40 such that a pocket or recess 73 is located radially inwards of the protrusion 45. Thus, the protrusion 45 is allowed to flex radially inwards to overcome splines 22, thereby providing a tactile and audible feedback to the user.

The nut 50 is provided between the inner body 20 and the driver 40. When referring to a last dose member, it may also be referred to the nut. As the same component is meant, the same reference numerals are used for the last dose member and the nut. The last dose member may be the nut.

External ribs 58 of the nut 50 engage splines 22 of the inner housing 20. An internal thread 55 of the nut 50 engages the external thread 46 of the driver 40. Further, in the embodiment of FIG. 14, four rotational last dose stop features 54 are provided on nut 50 for interaction with corresponding drive member stop features 48 on the driver 40.

The indication member 60 is a generally tubular element. The indication member 60 is preferably rotatable but axially constrained with respect to the inner housing by corresponding stops. The indication member 60 is interposed between the inner body 20 and the housing 10. A series of indicia 66, such as numbers providing dose information, is provided, e.g. printed, on the outer surface of the indication member 60. The numbers are arranged on a helical line such that only one number or only a few numbers are visible through window 123 at a time.

A sleeve-like part 72 of the button 70 with a reduced diameter extends in the distal direction and is inserted into the driver 40 such that a limited relative axial movement is allowed but relative rotation is prevented. This is achieved by a corresponding feature on the sleeve-like part 72 which is guided in the proximal opening (not explicitly indicated)

of the driver 40. A recess 73 which generally has the outline of the protrusion 45 is provided in the sleeve-like part 72 of button 70 (cf. FIG. 8).

The drug delivery device 100 further comprises a first movable member part 110*a* which, after an assembly of the drug delivery device 100, is preferably rigidly fixed to a second movable member part 110*b* in order to form a movable member 110 of the drug delivery device 100 (cf. in FIG. 1). When, in the following, it is referred to the movable member 110, it is referred to both components (110*a* and 110*b*) which are rigidly connected to each other. The movable member 110 has a sleeve-like shape with a longitudinal axis which, in an assembled state of the device, may coincide with the longitudinal axis x of the drug delivery device 100.

The two-component embodiment of the dose member 110 and the button 70 may, in collaboration with further components facilitate an easy assembly of the drug delivery device 100.

The drug delivery device 100 further comprises a display member 120. The display member 120 comprises a display member window 122. The movable member 110 may partly be received by the display member 120 when the drug delivery device 100 is assembled. The display member 120 is, preferably, rotationally locked with respect to the housing 10. The movable member 110 is at least partly received by the display member 120.

The drug delivery device 100 further comprises a spring member 130 (cf. FIG. 1). The spring member 130 is preferably connected to the inner housing 20 and the indication member 60. Alternatively, the spring member 130 may be connected to further components.

Figure 13:
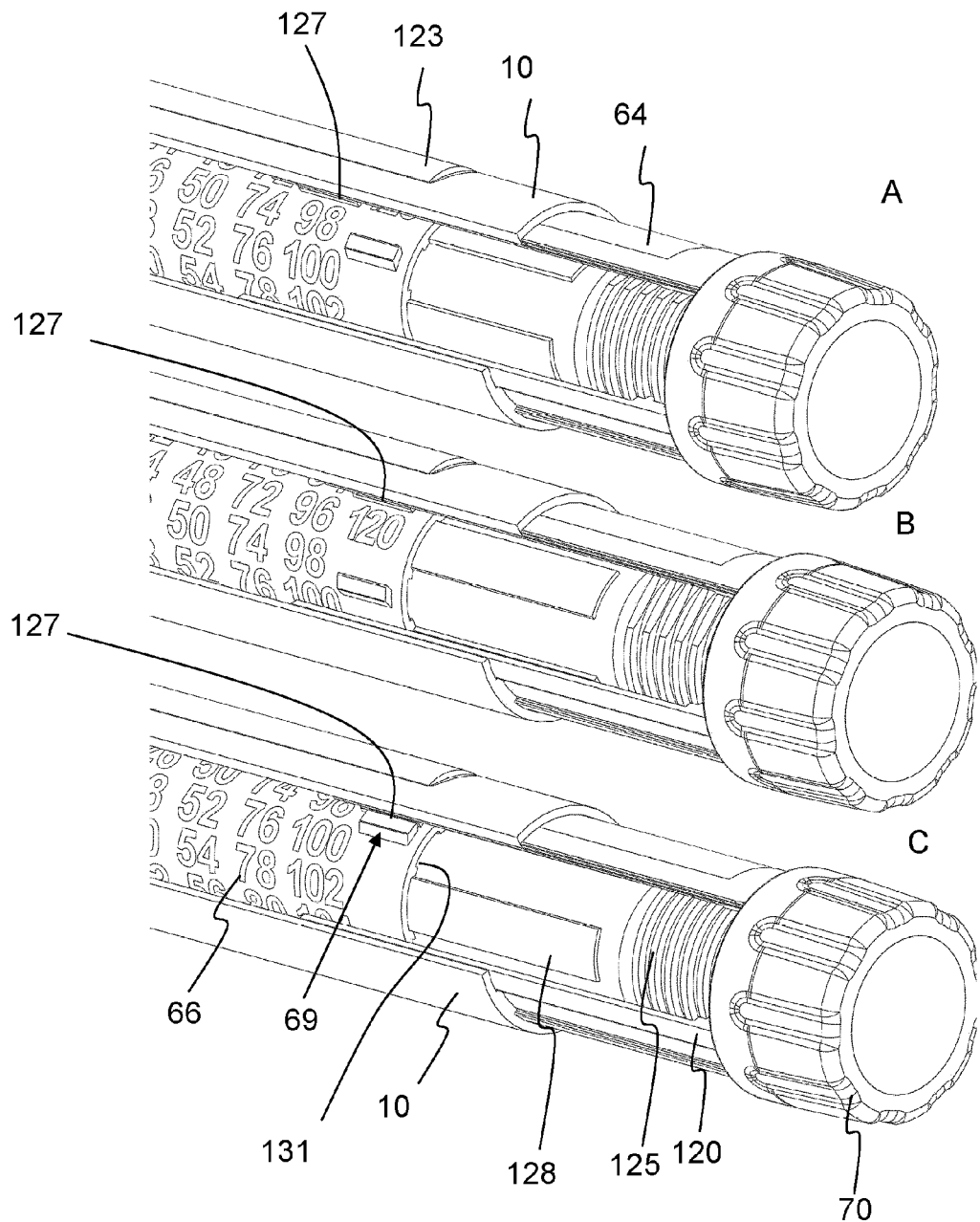

The movable member 110 is rotationally locked with respect to the indication member 60 via movable member splines 128 and indication member splines 131 (cf. FIG. 13). The movable member 110 is further threaded to the display member 120 via a movable member thread and a distal member thread (cf. 124, 125 in FIG. 8).

A releasable rotational locking mechanism is provided between the movable member 110 and the dose member 70 by corresponding locking teeth 114 and 74 (cf. FIG. 8). If teeth 74 of the button 70 engage locking teeth 114 of the movable member 110, the button 70 and the movable member 110 are rotationally locked. The resilient finger 44 of the driver 40 biases the button 70 in the proximal direction of the device 100, i.e. in a direction engaging the locking teeth 74, 114. In this situation, the drug delivery device is in a setting mode of operation, wherein the movable member 110 and the dose member 70 are rotationally locked.

The releasable rotational locking mechanism can be released, thereby allowing relative rotation by shifting the button 70 axially with respect to the housing 10 against the bias of finger 44, whereby the drug delivery device 100 is switched from the setting mode to a dispensing mode of operation.

Further, a dispense clicker is provided by flexible arms 65 on the movable member 110 and a toothed profile on the inner side of button 70.

FIG. 2 shows a drug delivery device 1 in the form of an injection pen. The device has a distal end 16 and a proximal end 17.

In FIG. 2, an indicium 66, particularly the number "0" is depicted by the drug delivery device 100 through the display member window 122 and the housing window 123. In FIG. 2, the drug delivery device is in an initial state, wherein no dose has been or yet been dispensed. The initial state may refer to an as-assembled state of the device. In this state, the moveable member 110, the display member 120 and the indication member 60 are preferably in an initial position. When a dose is set, said components are preferably in a dose set position.

In FIG. 2, the mentioned indicium 66 is shown at a distal end of the housing window 123. The display member window 122 is proximally confined by a colored section 64 of the display member 120. Said colored section may comprise a first color, such as, e.g. red color. A further colored section (not shown in FIG. 2; cf. 67 in FIG. 7C) may confine or adjoin the display member window 122 distally.

The drug delivery device 100 is preferably configured such that, for setting a dose, the user has to rotate the dose member 70 in a first direction with respect to the housing 10, wherein, the dose member 70 moves also proximally with respect to the housing 10. Preferably, the drug delivery device 100 is configured such that when a dose of drug is set, the display member window 122 travels proximally—originating from the position shown in FIG. 2—within the housing window 123. Unsetting or cancelling of a previously set dose may be carried out by the user in that the user rotates the dose member 70 in a second direction, opposite to the first direction, with respect to the housing 10. Preferably, any size of a dose of drug can be set and unset in predefined increments between zero and a predefined maximum dose.

The drug delivery device 100 may further be configured such that, In order to deliver a previously set dose, the user has to manually press or shift the dose member 70 distally with respect to the housing 10.

The drug delivery device 100 comprises a drive assembly further comprising a drive mechanism and a return mechanism. The drive mechanism may comprise or relate to the piston rod 30 and the drive member 40. The return mechanism may comprise or relate to the spring member 130.

The drug delivery device 100 further comprises a display assembly which may comprise or relate to the display member, the indication member and the movable member. The display assembly may further comprise a housing which may constitute the housing 10 of the drug delivery device 100.

FIG. 3 shows a partial longitudinal section of the drug delivery device 100 depicting components of the drive mechanism and the return mechanism (cf. also FIG. 8).

In FIG. 3, the drug delivery device 100 is in a state, wherein no dose has yet been set or dispensed and a bung or piston 82 retained in the cartridge 80 is arranged at the proximal-most end of the cartridge 80. The cartridge 80 includes a pre-filled, necked-down cartridge reservoir 81, which may be typically made of glass. A piercable rubber seal (not shown) is located at the other, distal, end. A crimped annular metal band 83 is used to hold the rubber seal in place. The cartridge 80 is provided within the housing 10 with piston rod 30 and bearing 31 abutting bung 82.

In FIG. 3, components of the device 100 are preferably at least partially concentrically arranged around the longitudinal axis x of the drug delivery device 100. The movable member 110 and also the indication member 120 are arranged in the initial position. Further, the last dose member 50 is in its distal-most position with respect to the drive member 40, indicating that no dose has yet been set and dispensed from the device by the user.

The indication member 60 is preferably axially constrained to the inner body 20 such that the indication member 60 preferably only rotates during an operation of the drug delivery device 100 without being axially moved. An operation of the device 100 may comprise setting and dispensing of a dose.

The spring member 130 is preferably a torsion spring. Preferably, the spring member 130 is comprised by the return mechanism.

Figure 4:
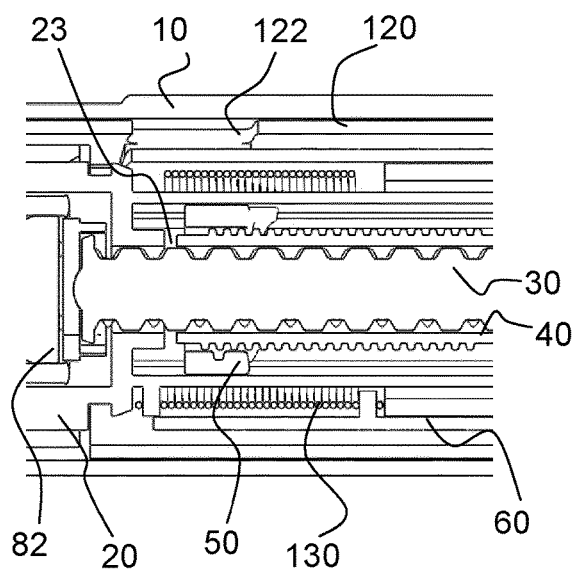
FIG. 4 shows a partial longitudinal section view of components of the drug delivery device.
Figure 5:
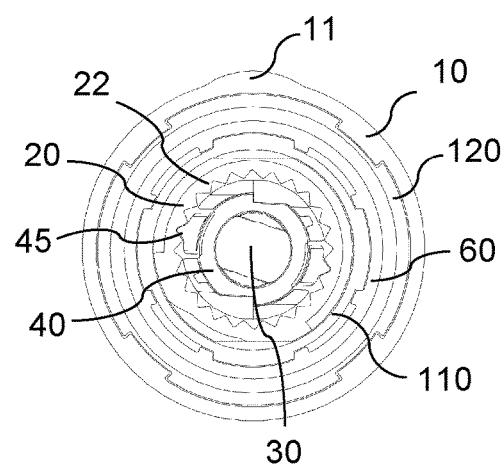
FIG. 5 shows a cross-sectional view of the drug delivery device.

FIG. 4 shows a section of the drug delivery device 100 of FIG. 3 in greater detail, thereby illustrating the location of the spring member 130. A distal end of the spring member 130 is connected to the inner housing 20 and a proximal end of the spring member 130 is connected to the indication member 60.

FIG. 5 shows a cross-sectional view of the drug delivery device 100. During setting of a dose, the dose member 70 is rotated along with the movable member 110, the drive member 40, and the indication member 60 in the first direction with respect to the housing 10. The movable member 110 is threaded to the inner housing 20 such that it also moves proximally with respect to the housing during setting of a dose. As the indication member 60 is rotated with respect to the housing, the spring member 130 is biased. Preferably, already in the initial state of the indication member 60, the spring member 130 is biased.

A torque of the spring member 130 must be overcome by the user when increasing the set dose. Said torque must be reacted by the splined interface (cf. splines 22 and protrusion 45) between the drive member 40 and the inner body 20 when the dose member 70 is rotated and a dose is set in the setting mode of operation. Said interface is arranged and configured such that the geometry of the splines 22 in the inner body 20 is biased to compensate for the nominal spring member torque such that torques relating to an increase of the set dose and a decrease of the set dose can be balanced or compensated, as the torque required to change the set dose is the sum of the torque to overcome the spring force of the spring member 130 which is positive when increasing the set dose and is negative when reducing the set dose, and the torque to overcome the splined interface.

Spline ramp angles of the splines 22 of the inner body 20 and the protrusion 45 on the drive member 40 are offset slightly to compensate for the effect of the spring torque of the spring member 130 during setting of a dose, such that the torque required to overcome the splined interface is greater when reducing the set dose than when increasing the set dose.

The splined interface between the splines 22 and the protrusion 45 may, alternatively, be configured symmetrical to provide the same overwinding torque when increasing or decreasing the set dose. Thereby, the spring member may be configured such that the torque may be considered small in comparison to typical user torques to change the set dose of drug delivery devices.

Figure 6:
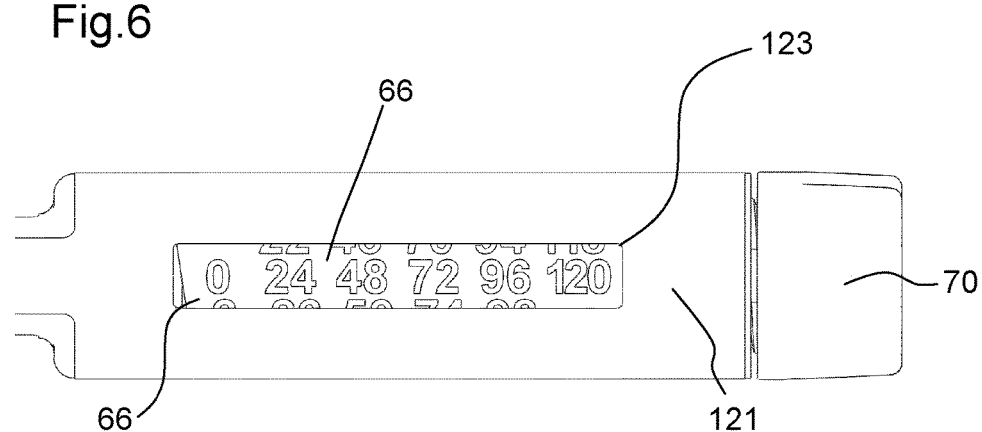
FIG. 6 shows a side view of components of a display assembly of the drug delivery device.

In FIG. 6, as compared to FIG. 2, the display member 120 is not shown such that indicia 66, particularly numbers indicating a quantity of drug, are displayed by the housing window 123. Next to the distal end of the housing window 123, "0" is indicated by the indication member 60 through the window 123. Next to the proximal end of the housing window 123, "120" is indicated by the indication member 60 through the window 123. The number "120" may relate to a maximum settable dose of the drug delivery device 100.

The housing window 123 may be lens-shaped such that indicia 66 which are visible through the housing window 123 are magnified. The housing 10 may be transparent. The housing window 123 may also be formed by a lens element (cf. 11 in FIG. 5) which may be unitarily formed by the housing 10 and which forms an elevated structure of the housing 10. The label 121 may be arranged and affixed to the housing 10 such that said lens element is arranged within the above mentioned aperture of the label 121.

The lens element 11 may axially extend over the full axial length of the indication member 60 in which indicia 66 are arranged, when the drug delivery device is assembled, as shown in FIG. 6. Preferably, the display member 120 is opaque such that indicia 66 not corresponding to the current dose indication of the drug delivery device are masked out by the display member and cannot be identified by the user.

FIGS. 7A-C show different states of a display assembly of the drug delivery device 100, respectively. Therein, the display member 120 is assembled to the device (as compared to FIG. 6) with the effect that only one indicium 66, preferably the indicium corresponding to the current dose set or dispensed, is visible to the user. The axial position of the display member window 122, which is visible through the housing window 123, provides a visual indication of the current dose status of the device to the user. The surface of the display member 120 may also provide further dose information of the drug delivery device 100.

In FIG. 7A, the indication member 60 and the display member 120 are in the initial position and a dose of zero units of drug is set, such that "0" is visible through the display member window 122. The display member window 122 is in a start position. The colored sections 64, is arranged proximally beside the display member window 122. The colored section 64 may comprise red color. The device 100 is preferably configured such that, when a dose is set, the display member window 122 travels proximally and, simultaneously, the indication member 60 rotates with respect to the housing 10 such that different indicia 66 are displayed through the display member window 122. It is shown in FIG. 7 that, thereby, the numbers indicating dose quantities are increased.

In FIG. 7B, a dose corresponding to four units or quantities of drug is set and "4" is displayed through the display member window 122, which is moved slightly proximally with respect to the housing, as compared to FIG. 7A.

In FIG. 7C, the maximum settable dose of 120 units of drug is set. In this case, the display member window 122 is arranged at its proximal-most position with respect to the housing 10, i.e. an end position of the display member window 122. Additionally, a further colored section 67 is displayed through the housing window 123 proximally beside the display member window 122. The further colored section 67 may comprise green color.

FIG. 8 shows a partial longitudinal section view of inner components of the drug delivery device 100. Therein, components of a drive assembly, comprising a drive mechanism and a return mechanism are shown in greater detail, as compared to FIG. 3, for example. It is shown that the movable member 110 comprises a movable member thread 125 and the display member comprises a display member thread 124 matching to the movable member thread 125. The movable member 110 further comprises an inner thread 160 matching to an outer thread 161 of the inner housing 20. Preferably, the lead of the threads 160, 161 defines or determines the axial distance (cf. D in FIG. 9) by which the dose member is moved distally with respect to the housing during setting of a dose.

The protrusion 45 of the drive member 40 is further shown in FIG. 8. An axial movement of the display member 120 relative to the housing 10 is generated by a combination of the thread engagement between the movable member 110 and the inner body 20 (cf. threads 160, 161) and the thread interface between the display member 120 and the movable member 110 (cf. threads 124, 125). Thus, said thread engagements, preferably enable a greater axial movement of the display member 120 with respect to the housing 10 to be carried out during setting of a given dose, than a corresponding axial movement of the dose member 70 with respect to the housing 10.

To this effect, the total distance, the display member 120 travels axially for one rotation of the dose member 70 may be a summation of the helical pitches of the thread 124 and the thread 161.

In FIG. 9, a longitudinal section view of the proximal end 17 of the drug delivery device 100 is shown. The figure shows the drug delivery device 100, wherein a comparatively large dose of drug is set, as the dose member 70 has already moved significantly proximally with respect to the housing 10. As compared to, for example, FIG. 8, a proximal end section of the display member 120 is arranged in an inner section 76 of the dose member 70. As the axial travel distance of the display member 120 during setting of a dose is greater than that of the movable member 110, the display member 120 increasingly axially overlaps the dose member 70 when the set dose is increased. In other words, during setting of a dose, the display member 120 is moved into the inner section 76, although, both components, i.e. the display member 120 and the dose member 70 move proximally with respect to the housing 10. To this effect, the inner section 76 is provisioned, which provides an accommodation for the display member 120 for set large doses without increasing the total length of the drug delivery device 100.

FIGS. 10A-C show perspective views of the drug delivery device 100, respectively, wherein the indication member 60 is visible through the housing 10. It is shown in FIG. 10A that no dose is set, as "0" is visible through the display member window 123. In FIG. 10B, a dose of 20 units of drug is set. In FIG. 10C, a maximum number of 120 units is set. Although, in this embodiment, a number of 120 units corresponds to the maximum settable dose, the drug delivery device 100 may also be configured such that more or less units of drug may be set and dispensed from the drug delivery device 100.

FIG. 11 shows a perspective view of the indication member 60. Indicia 66 are helically arranged around an outer surface of the indication member 60. It is further shown that the indicia 66 span a range from zero units to 120 units of drug. The indication member 60 further comprises a minimum stop feature 68 and a maximum stop feature 69 which are arranged beside the indicium indicating "0" and the indicium indicating "120", respectively, thereby adjoining the helical path of the indicia 66.

FIG. 12 shows a perspective view of the display member 120. Circumferentially beside the indication member window 122, a minimum dose stop feature 126 is provided, preferably affixed. At a side of the window 122, which faces away from the minimum dose stop feature 126, a maximum dose stop feature 127 is provided, preferably affixed. The display member 120 further comprises a projection 129. An outer surface of the projection 129 preferably comprises the further colored section 67. Said projection 129 is axially aligned with the display member window 122 with respect to the longitudinal axis x.

The minimum dose stop feature 126 is arranged and configured to interact with a minimum stop feature 68 such that axial movement of the display member 120 in a first axial direction with respect to the housing 10 is prevented when no dose is set. Thereby, the display member window 123 is arranged in a start position.

The maximum dose stop feature 127 is arranged and configured to interact with the maximum stop feature 69 such that axial movement of the display member 120 in a second axial direction, opposite to the first axial direction with respect to the housing 10 is prevented when a maximum settable dose of drug is set. Thereby, the display member window 123 is arranged in an end position.

The minimum dose feature 126 interacts with, preferably abuts the minimum stop feature 68 when no dose is set or when the user attempts to decrease the dose in this state. The maximum dose feature 127 interacts with, preferably abuts the maximum stop feature 69 when the maximum settable dose is set or when the user attempts to further increase the dose in this state. Said interactions may be illustrated in FIG. 13.

The relative position of said stop features (68, 69, 126, 127) limits the rotation of the indication member 60, as well as an axial movement of the display member 120 during a dose setting and/or dose dispensing operation. Said stop features (68, 69, 126, 127) may be formed by a protruding boss or shoulder protruding from a main body of the indication member 60 and the display member 120, respectively. Said stop features are arranged and configured such that the dose settable by the drug delivery device 100 is restricted to the range of indicia 66 on the display member 60 which corresponds to the range of settable doses.

In dose positions between zero and the maximum settable dose, the stop features 68, 69 pass under the display member 120 in sections of the length of the indication member 120, where no stop features are provided.

By embodying said stop features (68, 69, 126, 127) such that the display members 120 and the indication member 60 directly interact, an alignment of the indicia 66 to be displayed by the display assembly can be easily controlled.

Abutment radii of the indication member 60 and the display member 120 are, preferably, large such that reaction forces are low.

An abutment length can be maximised, as an axial travel of the display member 120 during an operation of the drug delivery device 100 is large.

FIGS. 13A-C further illustrate the mentioned stop functionality between the indication member 60 and the display member 120. In FIG. 13A, a dose of 99 units of drug (not explicitly indicated) may be displayed to the user. In FIG. 13B, a dose of 119 units of drug (not explicitly indicated) may be displayed to the user. In FIG. 13C, a maximum settable dose of 120 units of drug (not explicitly indicated) may be displayed to the user. Here, the maximum indication stop feature 69 abuts with the maximum display stop feature 127.

In FIG. 14, the last dose member 50 and a distal section of the drive member 40 is shown in a side view. The last dose member 50 comprises last dose stop features 54. The last dose stop features 54 are configured to interact with drive member stop features 48 of the drive member 40. The last dose member 50 is threaded to a distal end of the drive member 40. Therefore, the drive member 40 comprises a first outer thread section 46. The drive member 40 further comprises a second outer thread section 47. The last dose member 50 comprises a proximal inner thread 55 matching to the first thread 46 (cf. FIG. 15). Moreover, the last dose member 50 comprises a distal inner thread 56 matching to the second thread 47 (cf. FIG. 15). The lead of the second thread is greater than the lead of the first thread 46. The root diameter of the first thread 46 and the second thread 47 is, preferably, equal. The outer diameter of the second thread 47 is, preferably, greater than the first thread 46. The first and/or the second thread 46, 47 are, preferably, single start threads.

The last dose member is operable to be moved from a start position to an end position when, during an operation of the device 100, doses of drug are subsequently set and dispensed. The start position may relate to an arrangement of the last dose member 50 at a distal end of the drive member 40. The end position may relate to a position of the last dose member 50, wherein the last dose stop features 54 rotationally abut the drive member stop features 48, thus forming a rotational stop such that a further increase of the set dose is prevented.

The last dose member 50 is furthermore rotationally locked but axially movable with respect to the inner housing 20 (not shown in FIG. 14). To this effect, the last dose member 50 comprises ribs 58 which are axially guided by the housing splines 22 when the drive member 40 is rotated with respect to the housing 10.

Preferably, an axial extension of the dose stop feature is greater than a pitch or lead of the first thread section and less than a pitch of the second thread section. In FIG. 14, only half of a turn of the second thread is shown. Nevertheless, a pitch of the second thread may be determined by the double axial extension of the second thread 47, as shown in FIG. 14.

FIG. 15 shows a longitudinal section view of the last dose member 50. The last dose member 50 comprises a recess 57. The pitch of the distal thread 55 may be 0.7 mm and the pitch of the proximal thread 56 may be 6 mm. According to this embodiment, the overall device length of the drug delivery device 100 may be reduced by 6.5 mm, assuming a cartridge capacity of 450 units of drug. The mentioned numbers or values are not restrictive. Particularly, the length reduction of the device results from the first thread 46 being configured as a single start thread.

According to the provision of the first and the second thread, as mentioned, the stop features 48 and 54 can be embodied larger, i.e. with a longer axial extension. Thereby, stability of the last dose member 50 can be increased. This is due to the fact that, as the pitch is increased, when the last dose member 50 is moved proximally with respect to the drive member 40, said stop features can be embodied more robust. As the last dose member 50 moves proximally with respect to the drive member 40, e.g. during setting of a dose, at a certain point, the last dose member disengages from the first thread 46 and engages to the second thread 47.

The lead of the first thread 46 controls the axial travel of the last dose member 50 for the majority of the required rotation of the drive member 40, which occurs during dose setting only. Preferably, the second thread 47 controls the axial travel of the last dose member 50 for the final 180° of rotation of the drive member 40 during setting of a dose. Said embodiment of the two different threads allows to increase the size and strength of the stop features 48 and 54 such that stability is maintained. When the set dose corresponds to the amount of medicament remaining within the cartridge, the dose member stop features 54, preferably, abut the drive member stop features 48 such that a user is prevented from setting a greater dose.

As an alternative to the mentioned embodiment, the drive member 40 may also comprise only a single fine pitch thread (cf. first thread 46) in lieu of the mentioned first and second thread. This embodiment allows for a significant reduction of the axial space required for the movement of the last dose member 50 during an operation of the drug delivery device 100. This reduction enables a shorter overall device length or facilitates the accommodation of larger capacity drug cartridges.

During dispensing of a dose, the energy required to overcome the friction involved or caused by the movements of the indication member 60, the movable member 110 and the display member 120 is, preferably, expended by the return mechanism, particularly by the biased drive spring. Still further, the friction originating from a dispense clicker mechanism, as mentioned above, is provided by the return mechanism. During dose dispensing, the dispense clicker mechanism is active which involves button 70 and the movable member 110. The dispense clicker mechanism provides primarily audible feedback to the user that drug is being dispensed. The interaction between the flexible arms 65 on the movable member 110 and the toothed profile on the button 70 provides this dispense click. Relative rotation is only allowed in one direction. This occurs when the movable member 110 and the button 70 are decoupled during dispense and a click is produced for every unit of drug.

The torque exerted by the spring member 130 or required to bias the spring member 130 is preferably low, namely in the range of 0.5 to 2 Nmm. Said torque is required at the zero dose position and, as the spring member 130 is wound during setting of a dose, the torque increases to a maximum torque of e.g. 5 Nmm. The torque exerted by the spring member 130 is preferably chosen such that it has minimal impact on the setting torques the user has to expand during e.g. setting of a dose of drug.

By the provision of the return mechanism, the helical pitch of a threaded interface between the inner body 20 and the movable member 110 (threads 160, 161) can be reduced by 35%, as compared to a comparable embodiment in which no return mechanism is provisioned. To this effect, the axial travel of the movable member 110 for a given dose position or to set a given dose is reduced by 35%, as well.

When the axial travel of a movable member 110 is reduced as mentioned, the axial pitch between adjacent indicia 66 may reduce to approximately 4.3 mm which is considered insufficient for an easily readable state of the art display assembly, particularly for large set doses, which may require three digits, i.e. more than 100 units of drug. Therefore, the present disclosure provisions the functionality mentioned above relating to the inner section 76 of the dose member 70, wherein, during setting of a dose, the inner section accommodates a proximal end of the display member 120.

Reduction of the helical pitch of the threads 160, 161 is facilitated by the return mechanism mentioned above, as no portion of the axial force applied by the user during dispensing of a dose needs to be used to return the display member 110, the indication member 60 and the movable member 110 during dispensing of a dose. A torque must be applied to return, i.e. rotate, the indication member 60 and the movable member 110. In existing devices, without a return mechanism, this torque is generated by a portion of the axial force applied by the user overhauling or overcoming the threaded interface 160, 161. To overcome said interface, its lead angle must be sufficiently large to overcome frictional forces. This limits the scope to reduce the pitch of the threaded interface, particularly considering the susceptibility of the device to friction at this threaded interface.

With the given drive assembly, including the return mechanism, the drive mechanism is therefore significantly less susceptible or dependent to frictional losses at the threaded interfaces.

By reducing the axial travel of the movable member 110, also an ergonomic operation or design of the drug delivery device 100 is improved, particularly for large doses set or users with restricted digit motions. Reducing said axial travel distance (cf. D in FIG. 2) of the movable member 110, e.g. when a maximum dose of drug is set, also enables a reduction of the length of the piston rod 30 and the inner body 20 which, in turn, enables a shorter overall device length.

The torque provided by the spring member 130 during dispensing of a dose is particularly sufficient to rotate and/or return the movable member 110 via the indication member 60 and, thereby, to return and/or distally move the display member 120. It is also sufficient to overcome the dispense clicker provided between the movable member 110 and the dose member 70. Any remaining torque is applied to the threaded interface between the movable member 110 and the inner housing 20, which generates a small axial force at the axial coupling between the movable member 110 and the drive member 40. Therefore the spring member 130 may provide a small axial assistance force to the drive member 40 when a dose of drug is dispensed.

To use the device 100, a user has to select a dose by a rotation of the dose member 70 in the first direction. Due to the threaded engagement between the movable member 110 and the inner housing 20, the dose member 70 winds out of the device 100, as, in the setting mode of operation, the dose member 70 is rotationally locked with respect to the movable member 110. Additionally, the number of units is incrementally counted and displayed through the display member window 123 which also moves proximally with respect to the housing. Rotation of the button 70 in the first direction causes the driver 40 to rotate and in doing so it advances along the piston rod 30 which remains fixed throughout dialling. At the maximum settable dose, the stop features 69, 127 shown in FIGS. 11 and 12 abut to prevent further increasing the dose.

The last dose member or nut 50 provides the function of counting the total number of dispensed units. The nut 50 locks the device 100 at the end of life and as such no greater doses of drug can be dialled or set. The last dose nut 50 and the driver 40 are threadedly engaged with respect to each other, as explained above. Further, the last dose nut 50 is assembled into splines 22 as shown in FIG. 8 such that the nut 50 and the inner body 20 are rotationally locked together (at all times). Rotation of the indication member 60 via a rotation of the dose member during dialling biases the spring member 130. Further, the rotation of the piston rod causes the nut 50 to advance along the driver 40. The nut 50 is free to slide axially within the inner body 20 at all times which allows advancement of the nut 50. The change in threads (cf. 46, 47, 55, 56) shown in FIGS. 14 and 15 towards the final doses axially accelerates the advancement of the nut 50 towards the end of life lockout condition. At the end of life condition, the stop features 54 of the last dose nut 50 contact the corresponding features 48 on the driver 40. The splined contact with inner body 20 reacts any torque transmitted by these stop features 48.

With the desired dose dialled, the device 100 is ready for dose dispensing. This basically requires pushing button 70 distally which will result in a disengagement of the clutch or locking teeth 74, 114. As mentioned above, when dialling a dose, the button 70 is 'biased out' and the locking teeth 74, 114 which rotationally lock the movable member 110 to the button 70 are engaged. Upon pressing the button 70, the locking teeth 74, 114 disengage and relative rotation between the movable member 110 and the button 70 is possible (cf. FIGS. 3 and 8). In all conditions, the driver 40 and the button 70 are rotationally locked together by engagement. At the same time, the relative axial movement of the button 70 with respect to the driver 40 results in the pocket or recess 73 being shifted relative to the protrusion 45. Thus, the protrusion 45 is prevented from flexing inwards because the protrusion 45 rests on a non-recessed area (cf. recess 73) of button 70. In this condition, the driver 40 and the button 70 are rotationally constrained to the inner body 20, thus preventing any rotation relative to the housing 10.

With the desired dose dialled the button 70 can be depressed manually by the user to drive the drive mechanism to dispense a dose and the piston rod 30 is driven forward to dispense drug from the cartridge 80. Thereby, the driving force applied by the user is transferred to the piston rod via the drive mechanism to drive the piston rod 30 in the distal direction with respect to the housing 10.

The interaction of mating threads between the piston rod 30, driver 40 and the movable member 110 and the inner housing 20 may deliver a mechanical advantage of 2:1 or 3:1.

When the button 70 has been pressed and the device is in the dispensing mode of operation, the energy of the biased spring member 130 is used to drives the return mechanism, wherein the movable member 110 is rotated back in the second direction towards its initial position with respect to the housing. The above mentioned dispense clicker mechanism is also driven by the spring member 130. Particularly, the spring member 130 rotates the indication member 60 in the second direction towards its initial position with respect to the housing, wherein the indication member 60 is rotationally locked to the movable member via the splines 128, 131. As the display member 120 is threaded to the movable member 110, also the display member window 123 is axially returned or moved back, thereby instantaneously indicating the actual dose information during the dispensing operation.

Preferably, the spring force of the spring member 130 is smaller than the driving force required to operate the device in the dispensing mode of operation such that a dose of drug is dispensed.

In the presented concept of the drug delivery device 100, though not being explicitly described, also mechanisms may be applied with eliminate the necessity of a priming of the drug delivery device 100.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

10 Housing
11 Lens element
16 Distal end
17 Proximal end
20 Inner housing, inner body
22 Spline (inner body)
23 Inner thread (inner body)
30 Piston rod
31 Bearing 40 Drive member, driver
44 Resilient finger
45 Protrusion
46 First thread (dose member)
47 Second thread (dose member)
48 Drive member stop feature
50 Nut, last dose member
54 Last dose stop feature
55 Proximal thread (last dose member)
56 Distal thread (last dose member)
57 Recess (last dose member)
58 Rib (last dose member)
60 Indication member
64 Colored section
65 Flexible arm
66 Indicium
67 Further colored section
68 Minimum stop feature (indication member)
69 Maximum stop feature (indication member)
70 Dose member, button
72 Sleeve-like part
73 Recess (dose member)
74 Locking tooth (dose member)
76 Inner section
80 Cartridge
81 Cartridge reservoir
82 Piston, bung
83 Metal band
100 Drug delivery device
110 Movable member
114 Locking tooth (movable member)
120 Display member
121 Label
122 Display member window
123 Housing window
124 Display member thread
125 Movable member thread
126 Minimum dose stop feature
127 Maximum dose stop feature
128 Movable member spline
129 Projection
130 Spring member
131 Indication member spline
160 Inner thread (movable member)
161 Outer thread (inner body)
X Longitudinal axis
D Axial distance

The invention claimed is:

1. A drive assembly for a drug delivery device, the drive assembly comprising:
a housing having a proximal end and a distal end;
a drive mechanism comprising
  a piston rod, and
  a drive member to drive the piston rod to dispense a dose of drug, and
  a dose member coupled to the drive member, the dose member being movable to set the dose of drug;
a return mechanism comprising a spring member; and
a movable member which is coupled to the spring member,
wherein the drive assembly is configured such that in a setting mode of operation of the drive assembly, the movable member is coupled to the dose member and, during setting of the dose of drug, the movable member is movable from an initial position to a dose set position, thereby biasing the spring member,
wherein the drive assembly is configured such that, when the movable member is in the dose set position, the dose member is actuatable to switch the drive assembly from the setting mode of operation to a dispensing mode of operation of the drive assembly,
wherein the drive assembly is configured such that, in the dispensing mode of operation, the drive member and the movable member are decoupled such that the drive mechanism is operable by application of a driving force to the drive mechanism, and wherein the spring member of the return mechanism drives the movable member independently of the driving force towards the initial position of the movable member, and
wherein the drive assembly comprises a display member, wherein the display member is rotationally locked with respect to the housing, and wherein an axial distance by which the display member is moved is greater than an axial distance by which the dose member is moved, when the movable member is moved from the initial position to the dose set position.

2. The drive assembly according to claim 1, wherein the spring member is a torsion spring and the drive assembly is configured such that, during setting of the dose of drug, the movable member rotates in a first direction with respect to the housing and, during dispensing of the dose of drug, the movable member rotates in a second direction, opposite to the first direction, with respect to the housing.

3. The drive assembly according to claim 1, wherein the dose member is rotationally locked with respect to drive member, and wherein the drive assembly comprises a releasable clutch mechanism being configured such that, in the setting mode of operation, the dose member is rotatable with respect to the housing and, in the dispensing mode of operation, a clutch feature interacts with a complementary clutch feature such that the dose member is rotationally locked with respect to the housing.

4. The drive assembly according to claim 1, wherein the movable member is threadedly coupled to the housing, and wherein the drive assembly is configured such that an axial travel of the dose member during setting of the dose of drug is defined by threads which threadedly couple the movable member and the housing.

5. The drive assembly of claim 1, wherein, in the dispensing mode of operation, the driving force is transferred to the piston rod via the drive mechanism to drive the piston rod in a distal direction with respect to the housing.

6. The drive assembly of claim 1, wherein:
the movable member and the dose member are coupled via a releasable rotational locking mechanism,
the drive assembly is configured such that, in the setting mode of operation, the releasable rotational locking mechanism is engaged such that the movable member and the dose member are rotationally locked, and
the drive assembly is configured such that, in the setting mode of operation, the movable member is in the dose set position and the dose member is moved distally, the releasable rotational locking mechanism is disengaged such that the movable member and the dose member are free to rotate with respect to each other and the drive assembly is switched to the dispensing mode of operation.

7. The drive assembly of claim 1, wherein the drive assembly is configured such that energy stored in the spring member, when the movable member is in the dose set position, is used to drive the return mechanism and to drive a feedback mechanism operable to provide audible, visual and/or tactile feedback when the dose of drug is being dispensed.

8. The drive assembly of claim 1, wherein the drive assembly comprises an indication member, wherein the display member comprises a display member window and the indication member comprises indicia, and wherein the drive assembly is configured such that, during an operation of the drive assembly, the display member is moved axially with respect to the indication member such that different indicia are visible through the display member window.

9. The drive assembly of claim 1, wherein the dose member comprises an inner section, and wherein the drive assembly is configured such that, when the movable member is in the dose set position, a proximal end section of the display member is retained in the inner section, and wherein, when the movable member is in the initial position, the proximal end section is arranged outside of the inner section.

10. The drive assembly of claim 1, wherein a guiding element of the drive assembly comprises a first thread section with a first lead and a second thread section with a second lead being greater than the first lead, and wherein the drive assembly comprises a last dose member which is operable to be moved from a start position to an end position when the dose of drug is being increased, and wherein the last dose member is configured to interact with the first thread section when the last dose member is arranged in or near the start position, and wherein the last dose member is configured to interact with the second thread section when the last dose member is arranged in or near the end position.

11. The drive assembly according to claim 10, wherein the last dose member is configured to threadedly engage with the first thread section and the second thread section, and wherein the drive member comprises a drive member stop feature and the last dose member comprises a last dose stop feature which is configured to form a rotational stop with the drive member stop feature when the last dose member interacts with the second thread section such that a further increase of the set dose of drug is prevented.

12. The drive assembly of claim 10, wherein the first thread section and the second thread section are single start thread sections and an outer diameter of the second thread section is larger than an outer diameter of the first thread section.

13. The drive assembly of claim 1, wherein the spring member is coupled to the drive member and configured such that a spring force of the spring member is smaller than the driving force required to operate the drive mechanism in the dispensing mode of operation.

14. A drug delivery device comprising:
  a drive assembly comprising:
    a housing having a proximal end and a distal end;
    an inner body;
    a drive mechanism comprising a piston rod, a drive member to drive the piston rod to dispense a dose of drug, and a dose member coupled to the drive member, the dose member being movable to set the dose of drug;
    a return mechanism comprising a spring member; and
    a movable member which is coupled to the spring member,
  wherein the drive assembly is configured such that in a setting mode of operation of the drive assembly, the movable member is coupled to the dose member and, during setting of the dose of drug, the movable member is movable from an initial position to a dose set position, thereby biasing the spring member,
  wherein the drive assembly is configured such that, when the movable member is in the dose set position, the dose member is actuatable to switch the drive assembly from the setting mode of operation to a dispensing mode of operation of the drive assembly, and
  wherein the drive assembly is configured such that, in the dispensing mode of operation, the drive member and the movable member are decoupled such that the drive mechanism is operable by application of a driving force to the drive mechanism, and wherein the spring member of the return mechanism drives the movable member independently of the driving force towards the initial position of the movable member, and
  wherein the drive assembly comprises a display member, wherein the display member is rotationally locked with respect to the housing, and wherein an axial distance by which the display member is moved is greater than an axial distance by which the dose member is moved, when the movable member is moved from the initial position to the dose set position.

15. A drive assembly for a drug delivery device, the drive assembly comprising:
  a housing having a proximal end and a distal end;
  a drive mechanism comprising a piston rod and a drive member to drive the piston rod to dispense a dose of drug and a dose member coupled to the drive member, the dose member being movable to set the dose of drug;
  a return mechanism comprising a spring member; and
  a movable member which is coupled to the spring member,
  wherein the drive assembly is configured such that in a setting mode of operation of the drive assembly, the movable member is coupled to the dose member and, during setting of the dose of drug, the movable member is movable from an initial position to a dose set position, thereby biasing the spring member,
  wherein the drive assembly is configured such that, when the movable member is in the dose set position, the dose member is actuatable to switch the drive assembly from the setting mode of operation to a dispensing mode of operation of the drive assembly,
  wherein the drive assembly is configured such that, in the dispensing mode of operation, the drive member and the movable member are decoupled such that the drive mechanism is operable by application of a driving force to the drive mechanism, and wherein the spring member of the return mechanism drives the movable member independently of the driving force towards the initial position of the movable member, and
  wherein a guiding element of the drive assembly comprises a first thread section with a first lead and a second thread section with a second lead being greater than the first lead, and wherein the drive assembly comprises a last dose member which is operable to be moved from a start position to an end position when the dose of drug is being increased, and wherein the last dose member is configured to interact with the first thread section when the last dose member is arranged in or near the start position, and wherein the last dose member is configured to interact with the second thread section when the last dose member is arranged in or near the end position.

* * * * *

UNITED STATES PATENT AND TRADEMARK OFFICE
CERTIFICATE OF CORRECTION

PATENT NO. : 10,232,118 B2
APPLICATION NO. : 14/782657
DATED : March 19, 2019
INVENTOR(S) : Anthony Paul Morris Page 1 of 1

It is certified that error appears in the above-identified patent and that said Letters Patent is hereby corrected as shown below:

In the Claims

In Column 25, Line 54, Claim 1, after "rod," delete "and"

Signed and Sealed this
Twenty-fifth Day of June, 2019

Andrei Iancu
*Director of the United States Patent and Trademark Office*